(12) United States Patent
Alston

(10) Patent No.: US 11,826,313 B2
(45) Date of Patent: Nov. 28, 2023

(54) PROGRAMMABLE PILL DISPENSING DEVICE AND METHODS OF USE

(71) Applicant: Thomas Alston, Berlin, NH (US)

(72) Inventor: Thomas Alston, Berlin, NH (US)

(73) Assignee: Thomas Alston, Berlin, NH (US)

( * ) Notice: Subject to any disclaimer, the term of this patent is extended or adjusted under 35 U.S.C. 154(b) by 0 days.

(21) Appl. No.: 17/882,801

(22) Filed: Aug. 8, 2022

(65) Prior Publication Data

US 2023/0130729 A1    Apr. 27, 2023

Related U.S. Application Data

(63) Continuation of application No. 17/506,980, filed on Oct. 21, 2021, now Pat. No. 11,419,794.

(51) Int. Cl.
  *A61J 7/04* (2006.01)
  *A61J 7/00* (2006.01)
  *G16H 40/67* (2018.01)
  *G16H 20/13* (2018.01)

(52) U.S. Cl.
  CPC .......... *A61J 7/0427* (2015.05); *A61J 7/0069* (2013.01); *A61J 7/049* (2015.05); *G16H 20/13* (2018.01); *G16H 40/67* (2018.01); *A61J 2205/00* (2013.01)

(58) Field of Classification Search
  CPC ...... A61J 7/0427; A61J 7/0454; A61J 7/0481; G16H 20/13; G07F 11/44; G07F 11/24
  USPC ................... 221/268, 270; 700/236
  See application file for complete search history.

(56) References Cited

U.S. PATENT DOCUMENTS

| | | | | |
|---|---|---|---|---|
| 4,953,745 A | * | 9/1990 | Rowlett, Jr. | G07F 17/0092 221/7 |
| 5,884,806 A | * | 3/1999 | Boyer | A61J 7/02 221/9 |
| 6,163,736 A | * | 12/2000 | Halfacre | A61J 7/0481 221/185 |
| 7,004,351 B1 | * | 2/2006 | Boman | G07F 11/22 221/268 |
| 9,501,626 B2 | * | 11/2016 | Zhang | G16H 20/13 |
| 11,419,794 B1 | * | 8/2022 | Alston | A61J 7/0084 |
| 2010/0308070 A1 | * | 12/2010 | Clarke | G07F 11/44 221/277 |
| 2014/0214200 A1 | * | 7/2014 | Chrusciel | A61J 7/0076 221/15 |
| 2016/0220180 A1 | * | 8/2016 | Fateh | A61J 7/0427 |
| 2017/0132867 A1 | * | 5/2017 | Berg | A61J 7/0481 |

* cited by examiner

*Primary Examiner* — Timothy R Waggoner
(74) *Attorney, Agent, or Firm* — Caldwell Intellectual Property Law, LLC

(57) ABSTRACT

A programmable pill dispensing device, system, and methods are provided. A programmable pill dispensing device may be used to automatedly dispense a pill, such as a prescription medication, at a programmed predetermined time.

16 Claims, 8 Drawing Sheets

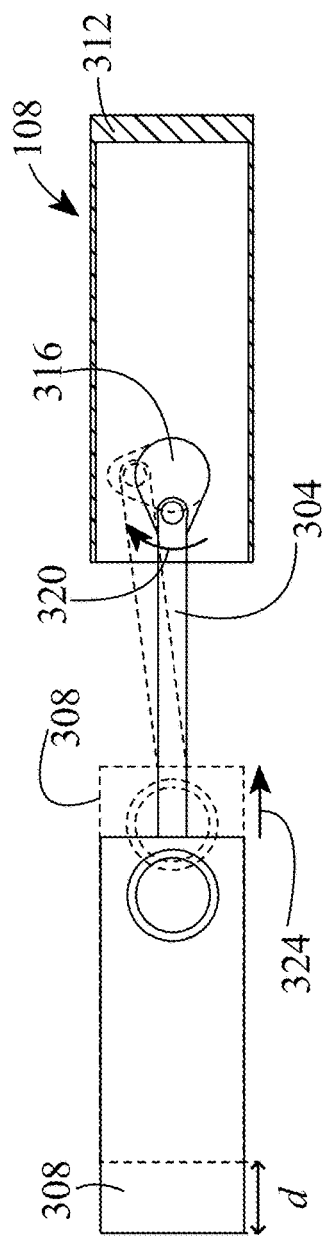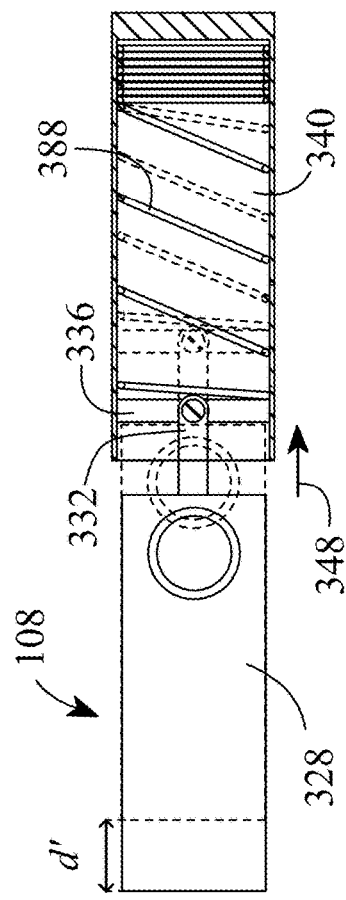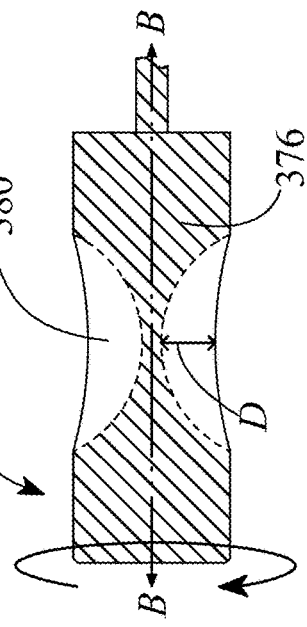

PROGRAMMABLE PILL DISPENSING DEVICE AND METHODS OF USE

CROSS-REFERENCE TO RELATED APPLICATIONS

This application is a continuation of Non-provisional application Ser. No. 17/506,980 filed on Oct. 21, 2021 and entitled "PROGRAMMABLE PILL DISPENSING DEVICE AND METHODS OF USE," the entirety of which is incorporated herein by reference. a

FIELD OF THE INVENTION

The present invention generally relates to the field of secured and automated dispensing. In particular, the present invention is directed to a programmable pill dispensing device.

BACKGROUND

Often consumers do not properly take prescription medications. Consumers make take the incorrect amount of a medication or forget to take a medication, which may be harmful or even lethal.

SUMMARY OF THE DISCLOSURE

In an aspect, a programmable pill dispensing device is provided, where the device includes a housing, which includes: a storage cavity contained within the housing and configured to store a pill; a channel, where the channel extends from the storage cavity; a sensor, wherein the sensor is configured to detect a quantity of pills disposed in the channel; and a tray connected to the channel. The device also includes a dispensing element, where the dispensing element is at least partially disposed within the channel and configured to dispense a pill when actuated. The device also includes a controller configured to actuate the dispensing element at a predetermine dispensing time and determine when the quantity of pills is less than a predetermined quantity threshold. Upon an actuation, the dispensing element moves so as to allow a pill to traverse through the channel and into the tray for retrieval by a user.

In another aspect, a method of automatedly dispensing a pill using a programmable pill dispensing device is provided, the method including storing pills in a storage cavity contained within a housing of a programmable pill dispensing device; detecting a quantity of pills disposed in the channel using a sensor; determining, using a controller, when the quantity of pills is less than a predetermined quantity threshold; actuating a dispensing element of the device at a predetermined time using a controller; dispensing, upon actuation of the dispensing element, a pill through a channel of the device, which extends from the storage cavity and is connected to a tray of the device, so that the pill traverses through the channel and into the tray; and alerting a user using an alarm transducer that the pill is dispensed and ready for retrieval by the user.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 3A-3D are diagrammatic representations illustrating various exemplary embodiments of a pill dispensing element in accordance with aspects of the invention;

DETAILED DESCRIPTION

At a high level, aspects of the present disclosure are directed to a programmable pill dispensing device, system, and methods. Administration of pills, such as prescription medications, is a crucial process that requires precision and care. A programmable pill dispensing device may assist primary care provider (PCPs), caregivers, or living assistance providers (LAPs) with managing medication administration throughout the day for a patient. Furthermore, a programmable pill dispensing device may eliminate any questions of whether a patient took a medication at the required time.

In the following description, for the purposes of explanation, numerous specific details are set forth in order to provide a thorough understanding of the present invention. It will be apparent, however, that the present invention may be practiced without these specific details. As used in this disclosure, the word "exemplary" or "illustrative" means "serving as an example, instance, or illustration." Any implementation described in this disclosure as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description in this disclosure, the terms "top", "bottom", "upper", "lower", "front", "rear", "right", "left", "vertical", "horizontal", and derivatives thereof shall relate to the invention as oriented in FIG. 1A. Moreover, terms such as "a", "an", and "the", and derivatives thereof shall be understood to mean "one or more" in this disclosure unless explicitly described as otherwise.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply embodiments of the inventive concepts defined in the appended claims. Hence, specific dimensions and other physical characteristics relating to the embodiments disclosed in this disclosure are not to be considered as limiting, unless the claims expressly state otherwise.

A "pill" may be any compact substance that may be consumed by swallowing, dissolving, chewing, or the like. For example, a pill may be a prescription medication, an over-the-counter medication, or a supplement, such as a vitamin supplement.

Figure 1A:
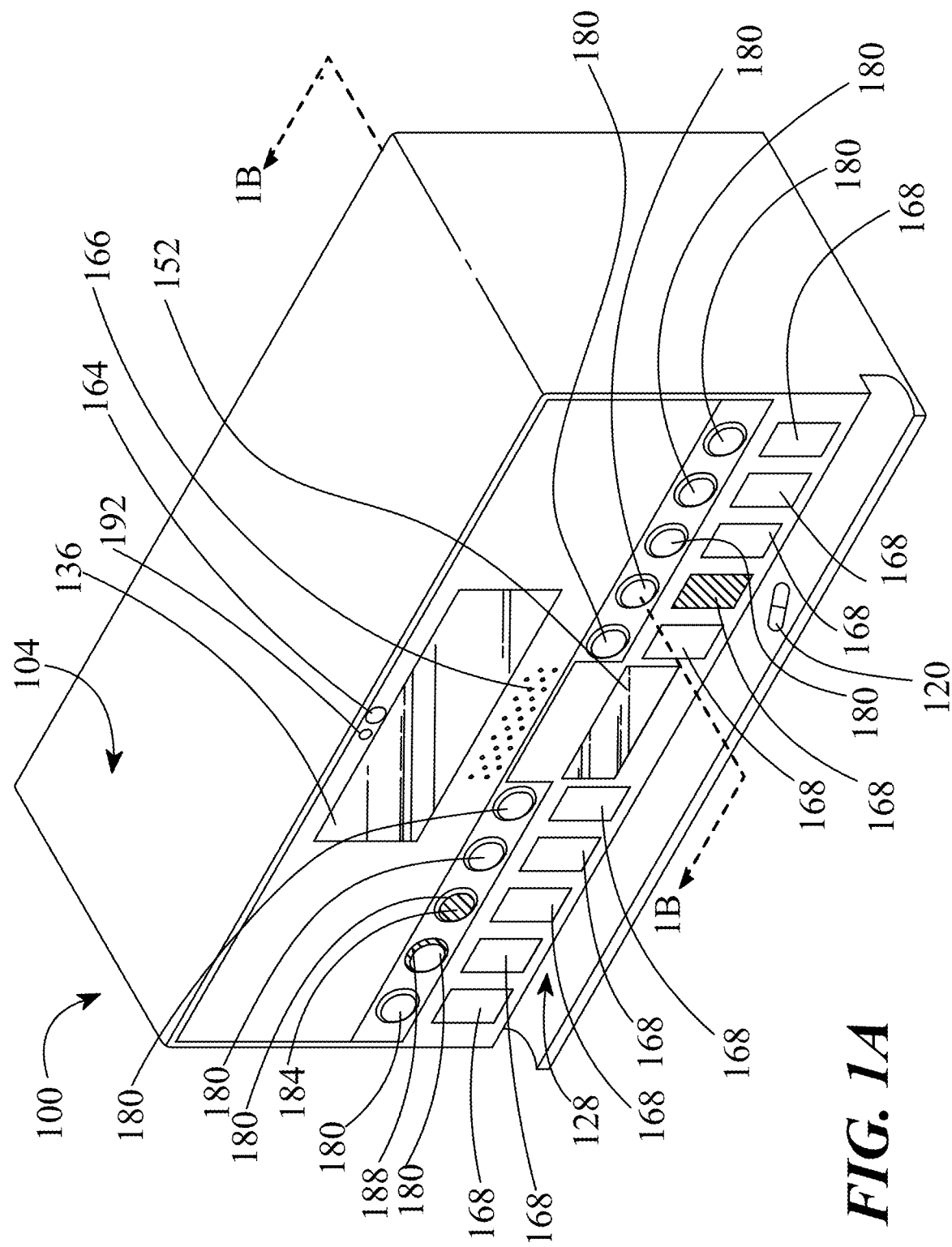
FIG. 1A is a diagrammatic representation illustrating an isometric view of an exemplary embodiment of a programmable pill dispensing device in accordance with aspects of the invention.
Figure 1B:
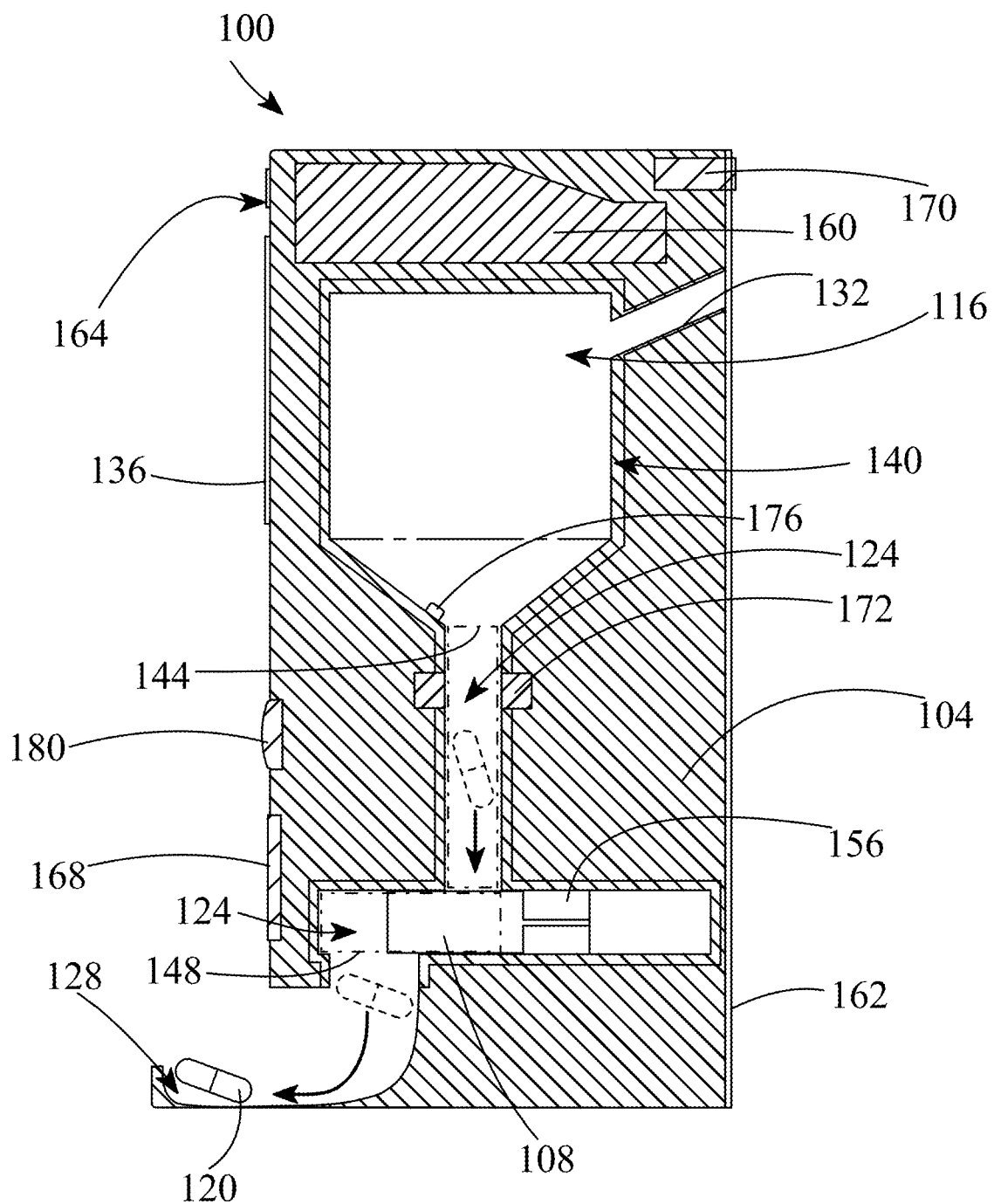
FIG. 1B is a diagrammatic representation illustrating a cross-sectional view of the exemplary embodiment of the programmable pill dispensing device taken along line 1B-1B of FIG. 1A in accordance with aspects of the invention.

Referring now to the drawings, FIGS. 1A and 1B illustrate an exemplary embodiment of a pill dispensing device 100 in accordance with one or more embodiments of the present disclosure. In one or more embodiments, pill dispensing device 100 (also referred to in this disclosure as a "device") includes a housing 104. Housing 104 may include a storage cavity 116 (also referred to in this disclosure as a "device"), which may be contained within housing 104 and configured to store pills 120. Housing 104 may also include a channel 124, which may be defined by housing 104 and may extend from storage cavity 116. Housing 104 may also include a tray 128 that is configured to hold a dispensed pill. Channel 124 may be connected to an opening of tray 128.

With continued reference to FIG. 1, housing 104 may provide a protective layer of material configured to create a barrier between internal components of device 100 and environmental components. In one or more embodiments, housing 104 may be constructed of materials and/or combinations of materials that may include metallic materials like aluminum, aluminum alloys, steel alloys, copper, tin, titanium, another undisclosed material, or a combination thereof. In one or more embodiments, housing 104 include nonmetallic materials alone or in combination with metallic components permanently or temporarily connected together. Nonmetallic materials that may be used alone or in combination in the construction of housing 104 may include high density polyethylene (HDPE), polypropylene, polycarbonate, acrylonitrile butadiene styrene, polyethylene, nylon, polystyrene, polyether ether ketone, or any combination thereof. Housing 104 may be manufactured by a number of processes alone or in combination, including but not limited to, machining, milling, forging, casting, 3D printing (or other additive manufacturing methods), turning, injection molding, or any combination thereof. One of ordinary skill in the art would appreciate that housing 104 may be manufactured in pieces and assembled together by screws, nails, rivets, dowels, pins, epoxy, glue, welding, crimping, or another undisclosed method alone or in combination. Housing 104 may include an injection molded component. The injection molded component may include a component manufactured by injecting a liquid into a mold and letting it solidify, taking the shape of the mold in its hardened form. In other embodiments, housing 104 may be made from fiberglass. In other embodiments, housing 104 may be made from a polymer. Such as, without limitations, housing 104 may be formed as multiple pieces or as a monolithic structure from a mold using plastic or resin. In one or more embodiments, housing 104 may include liquid crystal polymer, polypropylene, polycarbonate, acrylonitrile butadiene styrene, polyethylene, polyether ether ketone, and the like.

As understood by one skilled in the art, housing 104 may have various forms. For example, though housing 104 is shown as a rectangular structure in FIGS. 1A-1B, housing 104 may include other various shapes and sizes that allow housing 104 to contain one or more storage cavities 116. In one or more embodiments, housing 104 may be a monolithic structure. For instance, and without limitation, housing 104 may be a singular structure with cavity 116 and channel 124 integrated into housing 104. In other embodiments, housing 104 may include various components. For example, housing 104 may include a separate surface that defines cavity 116 so that cavity 116 may be individually removed from device 100. For instance, and without limitation, cavity 116 may be removed from device 100 so that, for example, a caregiver may refill storage cavity 116 with pills 120. In one or more embodiments, housing 104 may be made from various materials and using various methods, such as using a pour mold or casting. In an embodiment, housing 104 may be manufactured using additive manufacturing and/or 3D printing methodologies.

In one or more embodiments, housing 104 may include an access opening (not shown) with a housing panel 162 so that cavity 116 may be accessed by a user or medical professional. In one or more embodiments, an access opening may be located at the rear of housing 104. For instance, and without limitation, cavity 116 may be removed from device 100 through an access opening after unlocking panel 162. In other instances, and without limitation, cavity 116 may be filled with pills 120 using refill tube 132. For example, after opening panel 162, cavity 116 may be refilled with pills 120. Housing 104 may have a display 136 attached thereto, as discussed further below.

Figure 2:
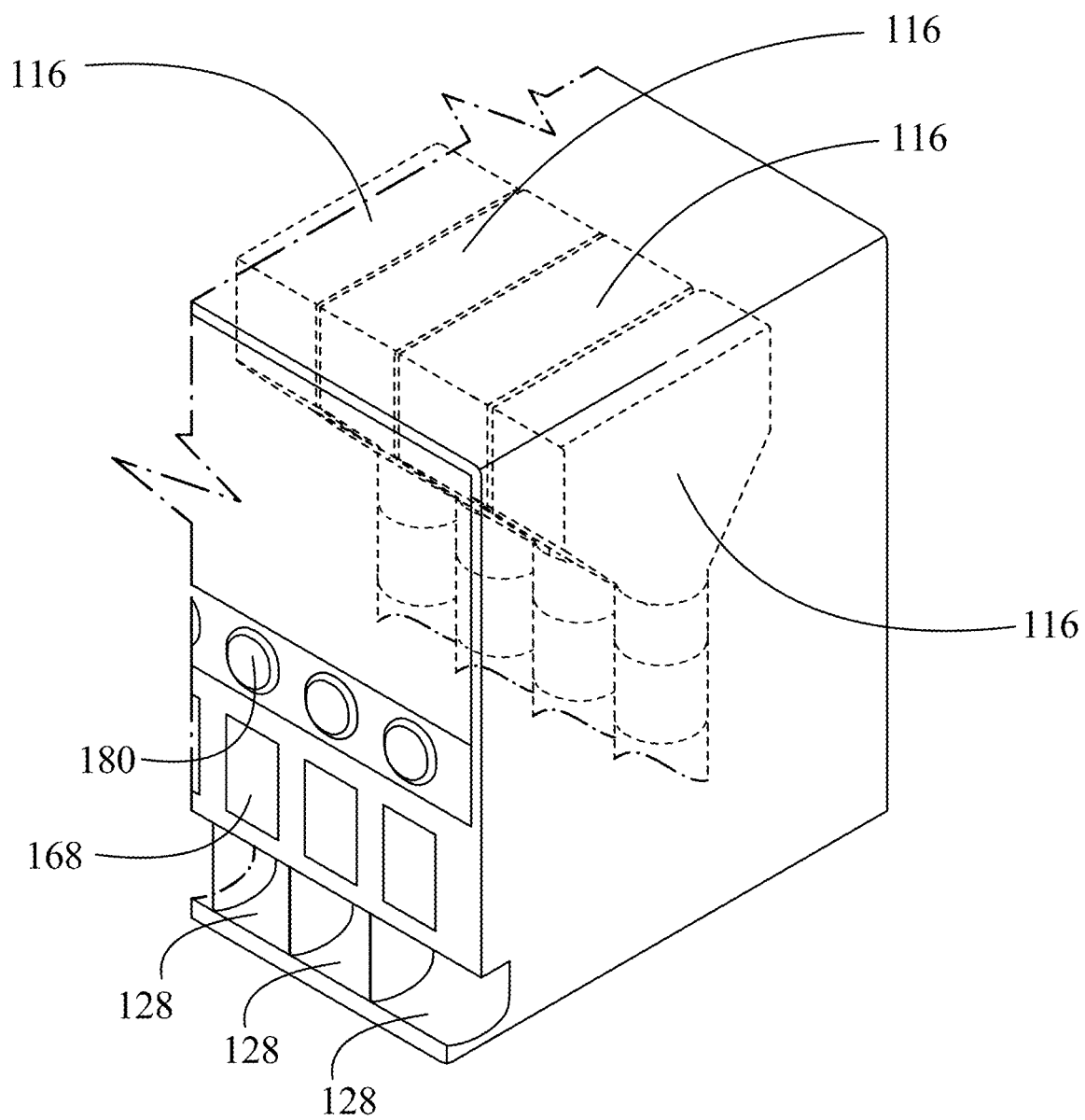
FIG. 2 is a diagrammatic representation illustrating a partially transparent isometric view of the exemplary embodiment of the pill dispensing device in accordance with aspects of the invention.

Still referring to FIGS. 1A and 1, in one or more embodiments, storage cavity 116 may be defined by an inner surface 140 of housing 104 (shown in FIG. 1). As understood by one skilled in the art, cavity 116 may include various shapes and sizes. Furthermore, housing 104 may define one or more cavities 116 therein. For instance, and without limitation, a plurality of cavities 116 may disposed within housing 104 and positioned adjacent to each other (as shown in FIG. 2). In one or more embodiments, storage cavity 116 and channel 124 may be integrate such that inner surface 140 is a monolithic piece of housing 104 that defines both storage cavity 116 and channel 124, storage cavity 116 and channel 124 may be separate components so that cavity 116 may be separated from housing 104 and/or channel 124 as a container. For example, inner surface 140 and cavity 116 may be removed from device 100 so that cavity 116 may be filled with pills 120 or cleaned.

Still referring to FIGS. 1A and 1B, in one or more embodiments, housing 104 of device 100 may include a channel 124, which may extend from cavity 116 and terminate at tray 128 (shown in FIG. 1i). In one or more embodiments, channel 124 may include one or more sections. For instance, and without limitation, channel 124 may have a first section 144 and a second section 148 (indicated by the dot-dash lines in FIG. 1), as discussed further below. As understood by one skilled in the art, channel 124 may include various shapes and sizes to accommodate different shaped and sized pills that may be stored in storage cavity 116 and traversed through channel 124. For instance, and without limitation, channel 124 may be cylindrical (as shown in FIG. 2). In one or more embodiments, channel 124 may be relatively straight. More specifically, second section 148 of channel 124 may be parallel and/or aligned with first section 144 of channel 124. In other embodiments, channel 124 may be angled. For instance, and without limitation, channel 124 may include a right angle therein (as shown in FIG. 1B) or an obtuse angle. More specifically, second section 148 of channel 124 may be oriented at an angle relative to first section 144 of channel 124. In other embodiments, channel 124 may be curved. As previously mentioned, channel 124 may be defined by inner surface 140 of housing 104.

Still referring to FIGS. 1A and 1, in one or more embodiments, housing 104 may include tray 128, which may be configured to receive dispensed pill 120. In one or more embodiments, tray 128 may be located near a bottom of housing 104. As understood by one skilled in the art, tray 128 may include various shapes and sizes. For instance, and without limitation, tray 128 may include an elongated trough, as shown in FIGS. 1A and 1B. In other instances, and without limitation, tray 128 may include, for example, a dish, such as a semi-circular dish. In other instances, and without limitation, tray 128 may include a plurality of individualized trays so that each tray 128 may be designated to a corresponding cavity 116 and channel 124. In one or more embodiments, tray 128 may be integrated into housing 104 or may be removable so that a user may, for example, choose a desired shape and size for tray 128, may clean tray 128, or may replace tray 128 if tray 128 is damaged.

In one or more embodiments, tray 128 may include a security enclosure (not shown). For instance, and without limitation, to ensure an unintended individual does not take or tamper with dispensed pill 120, tray 128 may include a sliding or hinged door. In one or more embodiments, security enclosure may be opened so that dispensed pill 120 may be retrieved from tray 128 by a pre-approved individual, such as the user or a caregiver, by using a security component, such as a fingerprint reader 152, a passcode, or a physical key. For example, a user may place their thumb on fingerprint reader 152 to unlock a security enclosure of tray 128 and retrieve dispensed pill 120 from tray 128. In one or more embodiments, tray 128 may be made of various materials. For example, tray 128 may include a polymer or a metal. In other embodiments, tray 128 may include a flexible material, such as such as silicon, to prevent pill 120 from sliding or bouncing off tray 128 when it is ejected from channel 124 onto tray 128.

Still referring to FIGS. 1A and 1B, in one or more embodiments, device 100 may include dispensing element 108 (shown in FIG. 1), which is configured to dispense pill 120 from storage cavity 116 into tray 128 when actuated. In one or more embodiments, dispensing element may be at least partially disposed within recess 156 of housing 104. Furthermore, dispensing element 108 may be disposed at least partially within channel 124. For instance, and without limitation, dispensing element 108 in an exemplary embodiment may move into an engaged position so that channel 124 is divided into a first section 144 and a second section 148, thus, blocking channel 124 and preventing any pills 120 from traversing through second section 148 of channel 124 to tray 128. In a disengaged position, dispensing element 108 may be moved toward recess 156 so that channel 124 is opened and thus first section 144 and second section 148 of channel 124 are communicatively connected so that at least one pill 120 may traverse from first section 144 to second section 148. In a disengaged position, dispensing element 108 may be moved so that channel 124 is partially open or completely opened, depending on the size and shape of pill 120. Though dispensing element 108 is described as a retractable dispensing element, as understood by one skilled in the art, dispensing element may include various shapes, sizes, and mechanisms. For example, dispensing mechanism 108 may include a retractable plug, a spring-loaded plug, a rotatable body, a slotted piece, a rotatable wheel, or the like, as discussed further below.

Still referring to FIGS. 1A and 1, in one or more embodiments, device 100 may include a controller 160. In one or more embodiments, controller 160 may be in communication with or control various components of device 100 or remote devices. For instance, and without limitation, controller 160 may be configured to actuate dispensing element 108 at a predetermined dispensing time. For example, controller 160 may be programmed to dispense a single pill at 7:15 PM EST. Thus, at 7:15 PM EST controller may actuate dispensing element 108 so that pill 120 may traverse through channel 124 and into tray 128 for retrieval by a user. Predetermined dispensing time may be recorded in memory of device 100 and/or accessible via electronic communication for device 100; for instance, predetermined time may be set using interface elements of device 100 and/or a user device, and may be stored in user device and/or device 100. Alternatively or additionally, device 100, user device, and/or a remote device may generate predetermined dispensing time using a machine-learning algorithm and/or model as described below, which may be trained using training examples correlating past retrievals to retrieval times, user entries logging past retrievals and/or times, or the like.

In one or more embodiments, controller 160 may include a user input and/or interface. For example, and without limitation, a user interface of controller 160 may include actuated components such as, for example, one or more buttons, knobs, joysticks, or slide bars. In another example, a user interface of controller 160 may include a display 136, which may be a touchscreen that may be actuated to provide an input signal from a user. Display 136 may include a graphic user interface (GUI) that a user may navigate using prompts to select desired commands and thus provide certain input signals, as discussed further below.

In one or more embodiments, controller 160 may include a memory component. In one or more embodiments, memory component may store information and data from various components of device 100. A memory component may include various types of memory devices including, but not limited to, volatile and non-volatile memory devices. For example, a memory component may include a volatile memory device such as DRAM (Dynamic random-access memory), SRAM (static random-access memory), or the like. In another example, memory component may include non-volatile memory such as ROM (Read-only memory), flash memory, EEPROM (Electrically erasable read-only memory), or the like.

In one or more embodiments, controller 160 may include a processor. A processor may be configured to interface and communicate with numerous components of device 100. For instance, without limitation, processor may communicate with a camera 164, sensors, display 136, status display 168, LEDs, dispensing element 108, storage cavities 116, and the like to perform methods described in this disclosure. In other embodiments, a processor may execute software instructions provided by, for example, a memory.

Still referring to FIGS. 1A and 1*i*, in one or more embodiments, device 100 may include one or more sensors, such as photoelectric sensor 172 and load cell sensor 176. For instance, and without limitation, device 100 may use a sensor to detect when the quantity of the pill 120 in storage cavity 116 and/or channel 124 is below a predetermined quantity threshold. For example, photoelectric sensor 172 may be configured to detect when a number of pills in storage cavity 116 is less than a predetermined quantity threshold. Photoelectric sensor 172 may include, for example, a thru-beam sensor, a retroreflective sensor, a diffused sensor, or the like. In another example, load cell sensor 176 may be configured to detect when a number of pills in storage cavity 116 is less than a predetermined quantity threshold. Load cell sensor 176 may include, for example, a miniature load cell sensor, beam load cell sensor, a canister style load cell sensor, or the like. A pressure sensor (not shown) may also be used to determine the amount of pills in storage cavity 116 and/or channel 124. Predetermined quantity threshold may depend, without limitation, on a type of pills, one or more elements of user data, and/or one or more elements of prescription information. Predetermined threshold may be retrieved from a database and/or lookup table using one or more elements of user data, and/or one or more elements of prescription information. Alternatively or additionally, a machine-learning process and/or model may be performed, generated, and/or loaded by device 100, a user device, and/or a remote device; such machine-learning process and/or model may be trained using training data correlating one or more elements of user data, and/or one or more elements of prescription information to one or more predetermined threshold values, which training data may be received from one or more users, experts, or the like.

Alternatively or additionally, and with continued reference to FIGS. 1A and 1, predetermined threshold may be implemented using a membership function of a fuzzy set as described below, where a degree of membership above a threshold value and/or matching one or more inferential rules may indicate that the threshold is met and/or exceeded. Threshold value, coefficients, weights, and/or biases of inferential rules, and/or coefficients, weights and/or biases of membership function and/or functions may include user-entered and/or stored values, and/or may be determined using one or more machine-learning processes, based for instance on training data correlating one or more elements of user data, and/or one or more elements of prescription information to one or more coefficients, weights, and/or biases of inferential rules, and/or coefficients, weights and/or biases of membership function and/or functions, which training data may be received from one or more users, experts, or the like.

In one or more embodiments, sensors 172,176 may be attached to housing 104. For instance sensors 172,176 may be attached to inner surface 140 of housing 104. For example, photoelectric sensor 172 may be attached to inner surface 140 and disposed within channel 124. In another example, inner surface 140 may be a transparent material that allows photoelectric sensor 172 to be attached to the outside of inner surface 140 while still operating as intended. In one or more embodiments, sensors 172,176 may be positioned in various locations within cavity 116 and/or channel 124 to detect the amount of pills 120 within storage cavity 116 and/or channel 124.

In one or more exemplary embodiments, pill quantity datum may be detected by sensors 172,176 and transmitted to controller 160 as an output signal. Controller 160 may then determine whether the amount detected is less than a predetermined quantity threshold set by, for example, user or medical personnel. If controller 160 determines an amount of pills 120 is less than a predetermined amount, controller 160 may notify a user or remote personnel. Additionally, if pill 120 is a prescription medication, controller 160 may communicate with remote personnel, such as with a pharmacist, to request a refill of prescription medication.

Though not shown, device 100 may include various other types of sensors. For instance, and without limitation, device 100 may include a motion sensor, a temperature sensor, thermocouples, thermistors, thermometers, infrared sensors, resistance temperature sensors (RTDs), semiconductor based integrated circuits (IC), a combination thereof or another undisclosed sensor type, alone or in combination. For instance, and without limitation, a temperature sensor may be used to detect if the temperature within device 100 has risen above or fallen below predetermined temperature thresholds.

Predetermined temperature threshold may depend, without limitation, on a type of pills, one or more elements of user data, and/or one or more elements of prescription information. Predetermined temperature threshold may be retrieved from a database and/or lookup table using one or more elements of user data, and/or one or more elements of prescription information. Alternatively or additionally, a machine-learning process and/or model may be performed, generated, and/or loaded by device 100, a user device, and/or a remote device; such machine-learning process and/or model may be trained using training data correlating one or more elements of user data, and/or one or more elements of prescription information to one or more predetermined threshold values, which training data may be received from one or more users, experts, or the like.

Alternatively or additionally, and with continued reference to FIGS. 1A and 1i, Predetermined temperature threshold may be implemented using a membership function of a fuzzy set as described below, where a degree of membership above a threshold value and/or matching one or more inferential rules may indicate that the threshold is met and/or exceeded. Threshold value, coefficients, weights, and/or biases of inferential rules, and/or coefficients, weights and/or biases of membership function and/or functions may include user-entered and/or stored values, and/or may be determined using one or more machine-learning processes, based for instance on training data correlating one or more elements of user data, and/or one or more elements of prescription information to one or more coefficients, weights, and/or biases of inferential rules, and/or coefficients, weights and/or biases of membership function and/or functions, which training data may be received from one or more users, experts, or the like.

Still referring to FIGS. 1A and 1B, pills 120 may be sensitive to extreme temperatures and spoil or lose efficacy if exposed to such temperatures. In an exemplary embodiment, if temperature sensor detects that the temperature within cavity 116 is higher than a predetermined temperature threshold, then a user may be notified. Temperature, for the purposes of this disclosure, and as would be appreciated by someone of ordinary skill in the art, is a measure of the heat energy of a system. Heat energy is, at its core, the measure of kinetic energy of any or all matter present within a system. Temperature, as read by any number or combinations of sensors present on sense board 404, may be measured in Fahrenheit (° F.), Celsius (° C.), Kelvin (° K.), or another scale alone or in combination. The temperature measured by sensors may comprise electrical signals which are transmitted to appropriate destination wireless or through a wired connection. Outputs from sensors or any other component present within device 100 may be analog or digital. Controller 160 may convert output signals from sensors to a usable form. The usable form of output signals from sensors, through controller 160 and of a processor of controller 160 may be either digital, analog, a combination thereof or an otherwise unstated form. Processing may be configured to trim, offset, or otherwise compensate the outputs of the at least a sensor. Based on sensor output, the processor can determine the output to send to a downstream component. A processor can include signal amplification, operational amplifier (OpAmp), filter, digital/analog conversion, linearization circuit, current voltage change circuits, resistance change circuits, or the like.

In one or more embodiments, device 100 may include a light-emitting diode (LED) indicator 180 to indicate a status of device 100. In one or more embodiments, LED indicators 180 might indicate low medication. For instance, and without limitation, device 100 may include a plurality of LED indicators 180 configured to indicate that sensors, such as photoelectric sensor 172 and/or load cell sensor 176, detect the number of pills 120 is less than the predetermined quantity threshold. Each storage cavity 116 may have a corresponding LED indicator 180 that shows when that specific storage cavity 116 has a low pill quantity. Sensors 172,176 may be programmable and adjustable since a type of pills stored in each cavity 116 may vary. In one or more embodiments, a size and weight of an individual pill may be provided to controller 160 via, for example, display 136 or a remote electronic device so controller 160 may program sensors 172,176 and adjust parameters of sensors 172,176 accordingly. When sensors 172,176 detect that storage cavity 116 is low in pills 120, then LED indicator 180 may illuminate to notify a user of the status of cavity 116. For example, LED indicator 180 may illuminate to indicate that cavity 116 has a number of pills lower that the predetermined quantity threshold and a refill is required. In addition, status display 168 may show a notification regarding the pill quantity in cavity 116 and may also include a notification if any steps have been taken by device 100 to assist with the low number of pills, such as contacting a pharmacist with a refill request.

In one or more embodiments, LED indicator 180 may include a dual-LED system. For example, as shown in FIG. 1A, LED indicator 180 may have a first LED 184 and a second LED 188. A dual-LED system may allow for a progressive status monitoring of a status of cavity 116 and/or channel 124. For instance, and without limitation, first LED 184 may illuminate to indicate that storage cavity 116 is empty as detected by, for example, pressure sensor, and second LED 188 may illuminate to indicate that channel 124 is low or empty on pills 120 as detected by, for example, an eye sensor or photoelectric sensor 172. First LED 184 and second LED 188 may be illuminated with the same color or varying colors. For example, first LED 184 may be yellow, and second LED may be red.

Still referring to FIGS. 1A and 1, in one or more embodiments, device 100 may include display 136, which is configured show a user information and allows user to interface with device 100. In one or more embodiments, display 136 may be attached to housing 104. In one or more embodiments, display 136 may show information about any pill stored in any cavity 116 of device 100. Information about a pill may include a name of a pill, a dosage of pill, an expiration date of pill, a next refill date of pill, a corresponding physician's name and contact information for pill, a refill alert for a pill, an image of pill, and so on.

In one or more embodiments, display 136 may be used to contact a remote device or individual using a communication component 196 of device 100, as discussed further below.

In one or more embodiments, display 136 may indicate status of device 100. For example, display 136 may show if device 100 is in a "secure" mode or an "unsecure" mode, as discussed further below. Display 136 may also show the status of cavity 116 and/or channel 124. For example, display may show an expected refill date or if cavity 116 and/or channel 124 is low on pills or empty.

In one or more embodiments, display 136 may provide menus and prompts that may be navigated to show various information or input various commands to be executed by controller 160. For example, display 136 may show contact information of important personnel, such as a caregiver, primary care physician (PCP), or emergency personnel. In one or more exemplary embodiments, display 136 may be used during communication. For example, display 136 may show an image, such as a picture or video, of a remote individual during a telephonic call. For example, a physician may be contacted using communication component 196 and a live-stream video of the physician during the call may be shown on display 136.

In one or more embodiments, display 136 may be a touchscreen. In one or more embodiments, display 136 may be foldable or hinged so that screen may be angled according to a user's preference. Display 136 may be various types of electronic visual displays. For instance, and without limitation, display 136 may include a liquid crystal (LCD) display, a light-emitting diode (LED) display, a plasma display, a quantum dot display, or other various types of video or monitor displays generally known. As mentioned in this disclosure, a processor of controller 160 may be configured to display a captured image on display 136.

In one or more embodiments, device 100 may include a status display 168. Status display 168 may be attached to housing 104. Status display 168 may show information regarding pills 120 in cavity 116. Status display 168 may also show information of pill, such as name of the pill type, contents, or the like so that a user may, at any time, know what type of pills is in which cavity 116. Information may include a name of a pill, a dosage of pill, an expiration date of pill, a next refill date of pill, a corresponding physician's name and contact information for pill, a refill alert for a pill, an image of pill, and so on. For instance, without limitation, status display 168 may provide a picture of dispensed pill 120 so that a user may know what pill to expect when retrieving pill 120 from tray 128.

Still referring to FIGS. 1A and 1, device 100 may include camera 164, which is configured to capture an image. In one or more embodiments, camera 164 may be configured to capture an image of a user. For instance, and without limitation, camera 164 may take a picture of a user when a motion sensor on a front of housing 104 and/or a pressure sensor on tray 128 detect that a dispensed pill 120 has been removed from tray 128. The capturing of the image may be to ensure that a user is picking up dispensed pill 120 and not an unintended individual, such as a child. In another instance, and without limitations, when an alarm transducer alerts a user that pill 120 has been dispensed into tray 128, camera may capture an image, such as a video recording, until dispensed pill 120 is retrieved. In other embodiments, when a user accesses tray 128 using, for example, fingerprint reader 152, camera 164 may capture an image of user. In one or more embodiments, an image of user may, for example, be transmitted to a caregiver so caregiver may confirm that user picked up pill 120, or the image may be stored in a memory of controller 160 for later retrieval by user or caregiver. In another exemplary embodiment, motion sensor 192 of device 100 may detect movement, the movement information signal may be sent to controller 160, and controller 160 may command camera 164 to capture an image. As previously mentioned, as an additional security measure to ensure an unintended individual does not take or tamper with dispensed pill 120, tray 128 may include one or more sliding or hinged doors that are locked until user placed finger on fingerprint reader 152 to gain access to tray 128. Camera 164 may allow remote monitoring using camera 164. For example, a caregiver may login and access camera 164 using a mobile device to monitor user.

In one or more embodiments, camera 164 allows for capturing of an image. For example, camera 164 may be used to take a picture or a video image. A processor may be configured to process captured images from camera 164 and store the image data information in a memory of controller 160 or provide the image on display 136 or status display 168 for viewing by a user. For example, a user may capture an image of a pill using camera 164 so that a processor may store the image data in a memory and retrieve the image data to show the image on status display 168 when, for example, the type of pill captured in the image is dispensed by device 100.

In one or more embodiments, a motion sensor 192 may be positioned near camera 164 so that a picture is taken when a user is detected in front of device. For example, if motion sensor 192 detects a presence in front of device 100 while dispensed pill 120 is in tray 128, camera 164 may take a picture as a security measure.

In one or more embodiments, device 100 may include fingerprint reader 152, which is configured to scan a fingerprint as a security measure. In one or more embodiments, a user may gain access to tray 128 using fingerprint reader 152, as previously mentioned in this disclosure. Fingerprint reader 152 may also be used to gain access to an opening of housing 104 (not shown). For example, a caregiver may have their finger scanned to unlock panel 162 of a rear opening in housing 104. In one or more embodiments, fingerprint reader may be attached to housing 104. In one or more embodiments, fingerprint reader 152 may be integrated into housing 104. In other embodiments, fingerprint reader 152 may be a separate component that is removeable from housing 104. For instance, without limitation, fingerprint reader 152 may be removed from housing 104 so that fingerprint reader 152 may be exchanged for a new fingerprint reader with upgraded hardware and/or software. Thus, fingerprint reader 152 may be upgraded without replacing entire device 100. In other embodiments, fingerprint reader 152 may be removed to be inserted into an updated model of device 100.

Still referring to FIGS. 1A and 1, device 100 may include speaker 166, which is attached to housing 104. In one or more embodiments, speaker 166 may be used to alert a user of when pill 120 has been dispensed into tray 128, as previously described in this disclosure. Speaker 166 may use a preselected sound or may announce the time and/or a predetermined retrieval time before device 100 contacts, for example, a caregiver. In one or more embodiments, speaker 166 may also be used in conjunction with communication component 196 to communicate with others, as discussed in this disclosure. Alert may announce pill 120 is in tray 128, if not picked up within, for example, 2 minutes of pill 120 being dispensed into tray 128 then device 100 may contact, for example, designated caregiver of user. A speaker 166 may project an alarm signal via sound and display 136 may project a visual alert. Speaker 166, display 136, LEDs 180-188, and/or any other component of device 100 capable of outputting a signal for a user to detect may act as an alarm transducer. An "alarm transducer," as used in this disclosure, is any component or set of components usable to convert an electronic or data signal into a user-detectable signal such as a display, audible noise, or the like. Alarm transducer may alternatively or additionally be any component of a user device which is suitable for use as an alarm transducer as described above.

In one or more embodiments, controller 160 may include a communication component 196. Communication component 196 may allow for device 100 to communicate the status of pill 120 to a remote device operated by remote personnel. For instance, and without limitation, communication component 196 may allow for communication between device 100 and a laptop, desktop, mobile phone, tablet, smart devices, or the like. Communication component 196 may use wired or wireless communication, as discussed in this disclosure. Communication component 196 may include various communication devices known in the art. Communication device may allow for interfacing between controller 160 and/or processor and various components of device 100 and/or communication may allow interfacing between controller 160 and/or processor and a remote device, such as a mobile phone or computer. Communication component 196 may also include a microphone. In an embodiment, communication component may include a computing device. Computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device may include a single computing device operating independently, or may include two or more computing device operating in concert, in parallel, sequentially or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software and the like) may be communicated to and/or from a computer and/or a computing device. Computing device may include but is not limited to, for example, a computing device or cluster of computing devices in a first location and a second computing device or cluster of computing devices in a second location. Computing device may include one or more computing devices dedicated to data storage, security, distribution of traffic for load balancing, and the like. Computing device may distribute one or more computing tasks as described below across a plurality of computing devices of computing device, which may operate in parallel, in series, redundantly, or in any other manner used for distribution of tasks or memory between computing devices. Computing device may be implemented using a "shared nothing" architecture in which data is cached at the worker, in an embodiment, this may enable scalability of system 100 and/or computing device.

With continued reference to FIG. 1, computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

In one or more embodiments, communication component 196 may be configured to facilitate a notifying of remote personnel if dispensed pill 120 has not been retrieved from tray 128 within a predetermined retrieval time. In one or more embodiments, a user may use communication component 196 to contact a caregiver, a pharmacist, a physician, emergency personnel, and so on. In other embodiments, a user may use communication component 196 to contact any other contact, such as a family member or friend. Predetermined retrieval time may depend, without limitation, on a type of pills, one or more elements of user data, and/or one or more elements of prescription information. Predetermined retrieval time may be retrieved from a database and/or lookup table using one or more elements of user data, and/or one or more elements of prescription information. Alternatively or additionally, a machine-learning process and/or model may be performed, generated, and/or loaded by device 100, a user device, and/or a remote device; such machine-learning process and/or model may be trained using training data correlating one or more elements of user data, and/or one or more elements of prescription information to one or more predetermined threshold values, which training data may be received from one or more users, experts, or the like.

In one or more embodiments, communication component 196 may be used for automated communication. For instance, and without limitation, controller 160 may use communication component 196 to contact a pharmacist after sensors 172,176 detect that a storage cavity 116 is low on a prescription medication and that a refill is required. A pharmacist may then receive the notification and fulfill the request for the new refill. Similarly, a pharmacist may then contact communication component 196 using a remote device and/or interface to notify a user that the request has been completed and that the refill is ready for pickup or being prepared for delivery.

In the case of a new prescription being required, communication component 196 may be used to contact the physician of the user and/or leave a notification for the user on status display 168 regarding a new prescription requirement.

In another exemplary embodiment, controller 160 may use communication component 196 to notify, for example, a caregiver, if a retrieval sensor, such as a pressure sensor, of tray 128, detects that dispensed pill 120 has not been retrieved by a user in the predetermined retrieval time. A retrieval sensor may be a photoelectric sensor, load cell sensor, or the like.

In one or more embodiments, communication component 196 may be used to provide an alarm, for instance via an alarm transducer, to a user, physician, and/or caregiver's electronic device to alert the user that one or more pills has been dispensed into tray 128. The predetermined retrieval time may also be displayed on the user's electronic device with an alarm signal. For example, a caregiver of the user may receive a notification on their mobile device via a graphic user interface that indicates pill 120 has been dispensed into tray 128. The information related to the pill may also be provided in the alert. Subsequently, a notification may be updated by telling the caregiver that the user has retrieved dispensed pill 120 from tray 128.

Still referring to FIGS. 1A and 1, device 100 may include a security component. In one or more embodiments, a security component may include a mechanical or electrical lock. For instance, and without limitation, a security component may include a physical lock 170 that requires a key to be opened. For example, storage cavity 116 may be locked with a physical lock to prevent undesired access to pills 120 contained within cavity 116. In other embodiments, display 136 may require a passcode be entered in order for access to cavity 116 and/or tray 128 to be gained. In one or more embodiments, a security component may include a security sensor (not shown) configured to detect when storage cavity 116 has been accessed or a physical lock has been tampered with. In one or more embodiments, a security component may include fingerprint reader 152, which may be used to unlock device 100, as previously described in this disclosure. For example, display 136 may prompt a user to place their thumb on fingerprint reader 152 to unlock panel 162 of device 100 and gain access to storage cavities 116 and/or tray 128.

In one or more embodiments, device 100 may be programmed to have a "secured" or "unsecured" mode. For example, if device is in a secured mode, cavities 116 cannot be accessed with using, for example, fingerprint reader 152 or unlocking lock 170, and communication component 196 may send out an alert if tampering with device 100 is detected by a security component. If device 100 is in an unsecured mode, then storage cavities 116 and/or tray 128 may be readily accessed without using a security component.

In one or more embodiments, a security component may include a "fail-safe" mode. In a fail-safe mode, if device 100 loses power while in a secured mode, device 100 will remain secure to prevent tampering with storage cavities 116.

In one or more embodiments, device may be powered by a battery or by using a plug. In one or more embodiments, a rechargeable lithium-ion battery may be used as a power source. In one or more embodiments, device 100 may have a plug and be compatible with 120 V electrical systems. In one or more embodiments, battery may be used as a backup power source in case power to a plug of device 100 is no longer supplied, such as during a power outage. In case of complete power failure of device 100, a key may be used to unlock housing panel 162 and access pills 120.

Now referring to FIG. 2, a partially transparent isometric view of an exemplary embodiment of device 100 with a plurality of storage cavities 116 is shown in accordance with one or more embodiments of the present disclosure. In one or more embodiments, device 100 may include a plurality of storage cavities 116, where each cavity 116 may be filled with a different type of pill 120 that may be dispensed at various predetermined times. In one or more embodiments, each storage cavity 116 may be communicatively connected to a corresponding status display 168, LED indicator 180, and sensor, such as sensors 172,176.

FIGS. 3A-3D illustrate various exemplary embodiments of dispensing element 108 in accordance with one or more embodiments of the present disclosure. FIGS. 3A and 3B are partial cross-sectional views of exemplary embodiments of dispensing element 108 as a retractable dispensing element. As shown in FIG. 3A, dispensing element 108 may include a plug 308 moveably attached to an arm 304. Arm 304 may be attached to a lumen 312 by a pivot point 316. Rotation of pivot pint 316 may move arm 304 and, thus, move plug 308 in a relatively lateral movement, such as toward and away from lumen 312. For example, rotation of pivot point 316 by, for example, controller 160 moves plug 308 fore and aft within recess 156 (shown in FIG. 1). As plug 308 moves fore and aft within recess 156, pills 120 may be dispensed. For instance, and without limitation, when pivot point 316 is rotated in a first direction, as indicated by arrow 320, plug 308 may be moved toward lumen 312, as indicated by arrow 324, creating a distance d within channel 124 (between inner surface 140 and plug 308) wide enough to allow a single pill to pass plug 308 and traverse through channel 124 to tray 128.

As shown in FIG. 3B, dispensing element 108 may be a spring-loaded retractable element. Plug 328 may connected to an arm 332, which is fixedly connected to a platform 336 that is slidably disposed within a lumen 340. Platform 336 may be abutting a spring 388 that may be compressed or expanded. Plug 328 may be moved fore and aft within recess 156 (shown in FIG. 1B) when platform 336 is moved fore and aft within lumen 340. When plug 328 is retracted toward lumen 340 (as indicated by arrow 348), a distance d' is created between inner surface 140 and plug 328 that is wide enough for a single pill to pass plug 328 and traverse through channel 124 and into tray 128.

As shown in FIGS. 3C and 3D, dispensing element 108 may also be a rotational dispensing element. As shown in FIG. 3C, dispensing element 108 may include a body 352, which has a thread 356 extending therefrom. Thread 356 may have a root 360 between crests 364 of thread 356. A width w of root 360 may be such that pill 120 may be seated within root 360 and abutting flanks 368 of thread 356. Thread 356 may also include a height h that allows pill 120 to be recessed within thread 356 and thus below height h of thread 356. Body 352 may be rotated about a central axis A of body 352 to move pill 120 through channel 124 and ultimately into tray 128. For instance, and without limitation, body 352 may be rotated about central axis A so that pills 120 disposed within thread 356 are advanced in a direction parallel to central axis A with each revolution of body 352 about central axis A. Thus, in an exemplary embodiment, a single pill may be traversed through channel 124 with, for example, each quarter revolution of body 352.

As shown in FIG. 3D, dispensing element 108 may be a rotatable dispensing element with a body 376, which includes an indentation 380. Indentation 380 may be sized so that pill 120 may be at least partially seated within depth D of indentation 380 so that when body 376 rotates about a central axis B of body 376, pill 120 may be rotated about central axis B. Thus, in an exemplary embodiment, when body 376 is rotated, for example, a half rotation, pill 120 may be moved from a first section 144 of channel 124 to a second section 148 of channel 124 and into tray 128. The rotatable dispensing element 108 of FIG. 3D may also be combined with a retractable component of, for example, dispensing elements 108 of FIGS. 3A and 3B. For example, pill 120 may be completely seated into indentation 380, body 376 may then be moved away from recess 156 and rotated so that pill is then dropped into second section 148 of channel 124 (shown in FIG. 1).

As understood by one skilled, dispensing element 108 may be various sizes and shapes without changing the scope or spirit of the invention. For example, dispensing element 108 may be a pin wheel, two slidable surfaces with slots that may be aligned to allow a pill to traverse through the aligned slots of the surfaces, or the like. Also, understood by one skilled in the art, the proportions of dispensing element 108 may be adjusted according to the size and shape of pill 120. In one or more embodiments, dispensing element 108 may be interchangeable and thus removed and replaced with other types of dispensing elements as desired.

Figure 4:
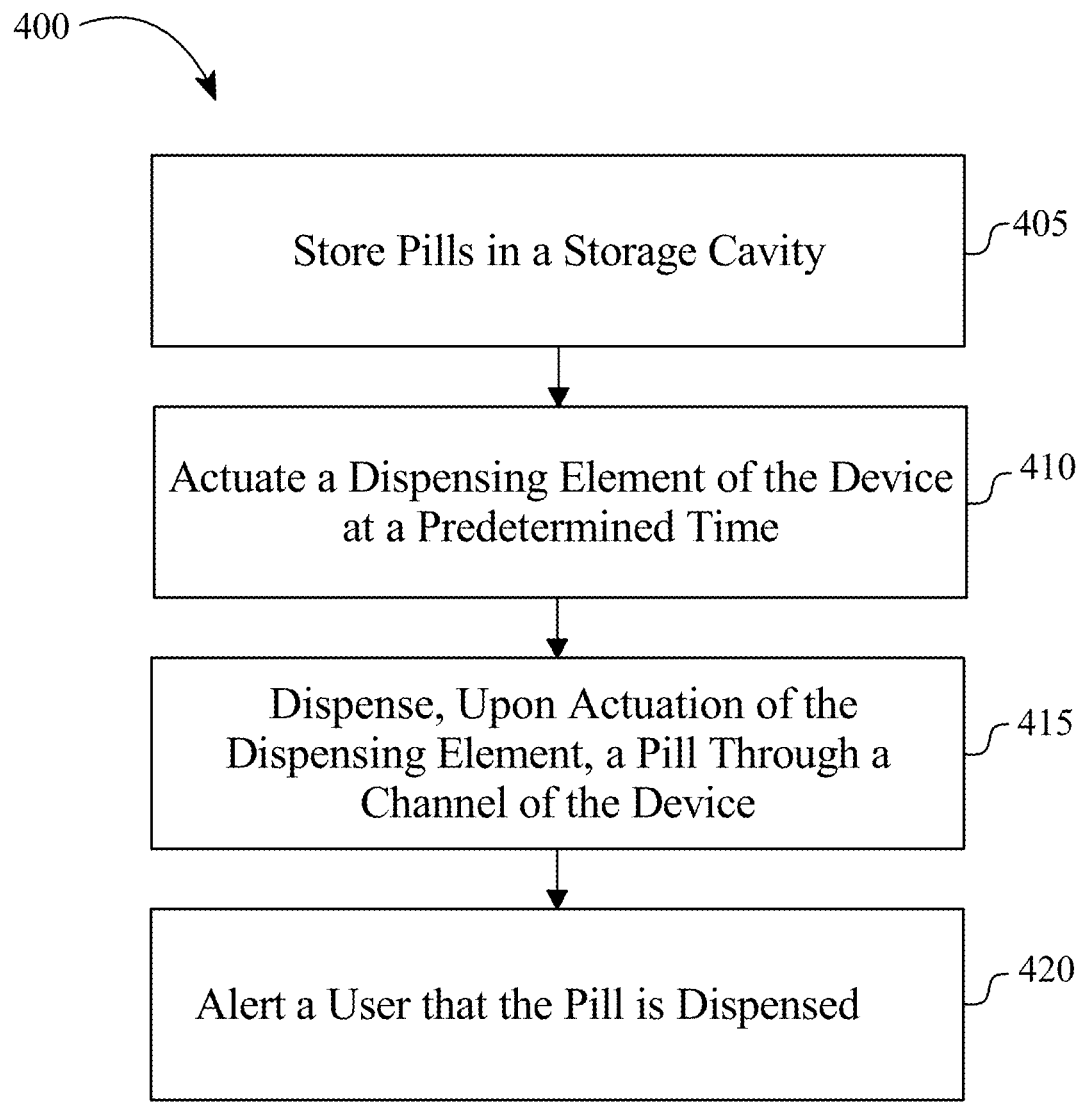
FIG. 4 is a flow diagram illustrating an exemplary method of automatedly dispensing a pill using the exemplary embodiment of the programmable pill dispensing device.

FIG. 4 is a flow chart showing a method 400 of automatedly dispensing pill 120 using programmable pill dispensing device 100. As shown in block 405, method 400 includes storing pills 120 in storage cavity 116, which is defined by housing 104 of device 100.

As shown in block 410, method 400 includes actuating dispensing element 108 of device 100 at a predetermined time using controller 160.

As shown in block 415, method includes dispensing, upon actuation of dispensing element 108, pill 120 through channel 124, which extends from storage cavity 116 and is connected to tray 128, so that pill 120 traverses through channel 124 and into tray 128. Method 400 may further include detecting, by at least sensor, when a number of pills 120 in storage cavity 116 is less than a predetermined quantity threshold. In one or more embodiments, sensor may include at least sensors 172,176. Method 400 may further include indicating, by light-emitting diode (LED) indicator 180, that a sensor detects a number of pills 120 is less than the predetermined quantity threshold.

As shown in block 420, method 400 includes alerting, user an alarm transducer, a user that pill 120 is dispensed and ready for retrieval by a user. Method 400 may further include notifying, by communication component 196, a remote personnel that dispensed pill 120 has not been retrieved from tray 128 within a redetermined retrieval time. Method 400 may further include, by a communication component, facilitating communication between device 100 and remote personnel.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
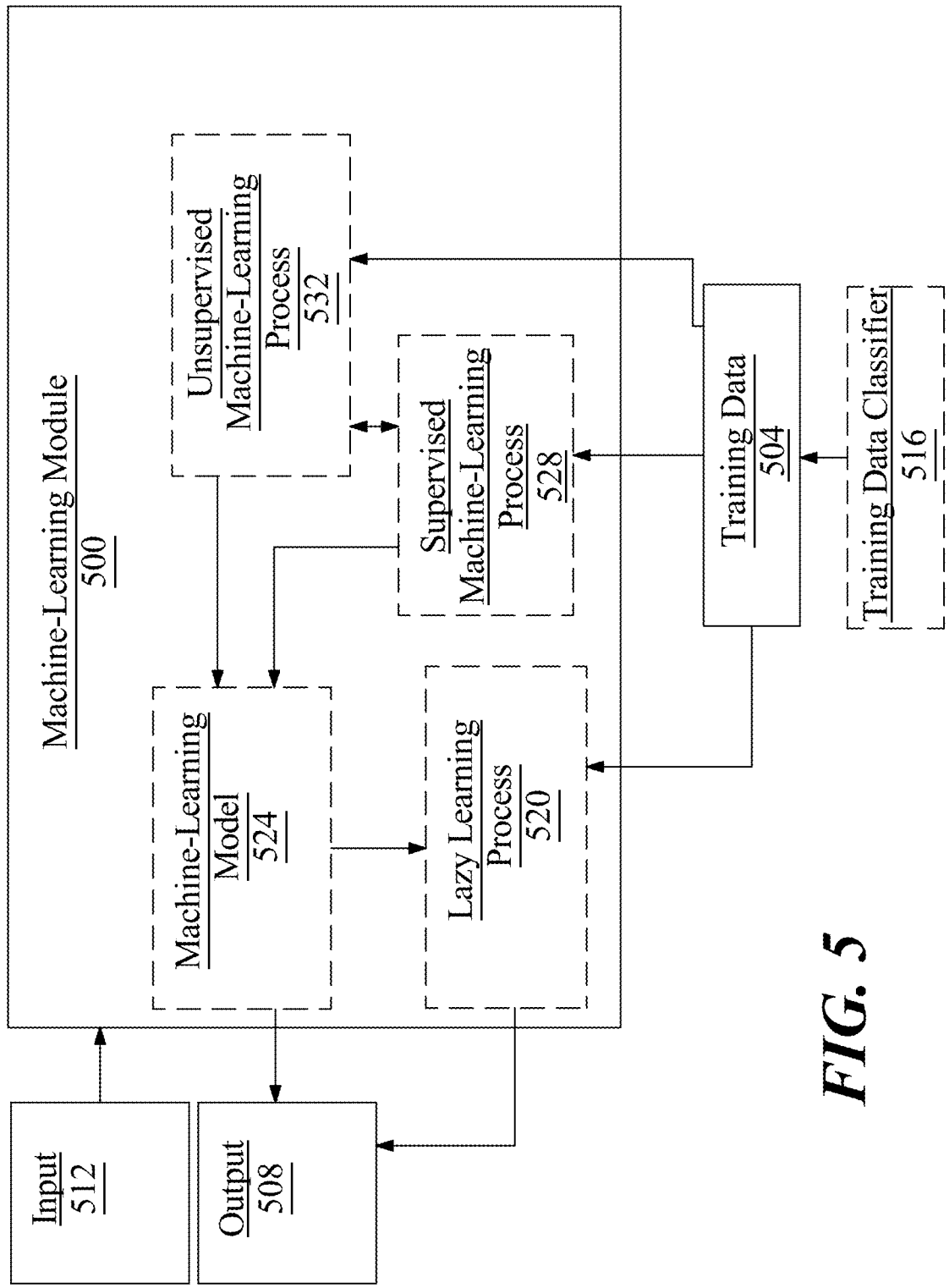
FIG. 5 is a block diagram illustrating an exemplary machine-learning module that can be used to implement any one or more of the methodologies disclosed in this disclosure and any one or more portions thereof in accordance with aspects of the invention.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process", as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 604 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a process whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors' classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors' algorithm, a lazy naive Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include user signals as described above as inputs, autonomous functions as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naive Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

In one or more exemplary embodiments, machine learning may be used to, for example, detect when a user is noncompliant or when a user misses a dose. For example, and without limitation, an input 512, such as type of pill stored in cavity 116, may be inputted into machine-learning module 500, which may in turn provide output 508, such as predetermined times that a pill should be administer and thus dispensed from device 100, predetermined retrieval times, and/or alarm settings. In one or more exemplary embodiments, training data set 504 may include data associated with the type of pill, such data regarding a dosage amount, a visual representation of the pill, chemical composition of the pill, and so on. In one or more embodiments, machine-learning module 500 may also be used to detect when a user takes a dose, or accesses pill 120 of storage cavity 116, outside of the predetermined time. In other embodiments, machine-learning module 500 may be used to detect when pill 120 has not been retrieved from device 100 and remote personnel must be notified and/or camera 164 should be activated.

Figure 6:
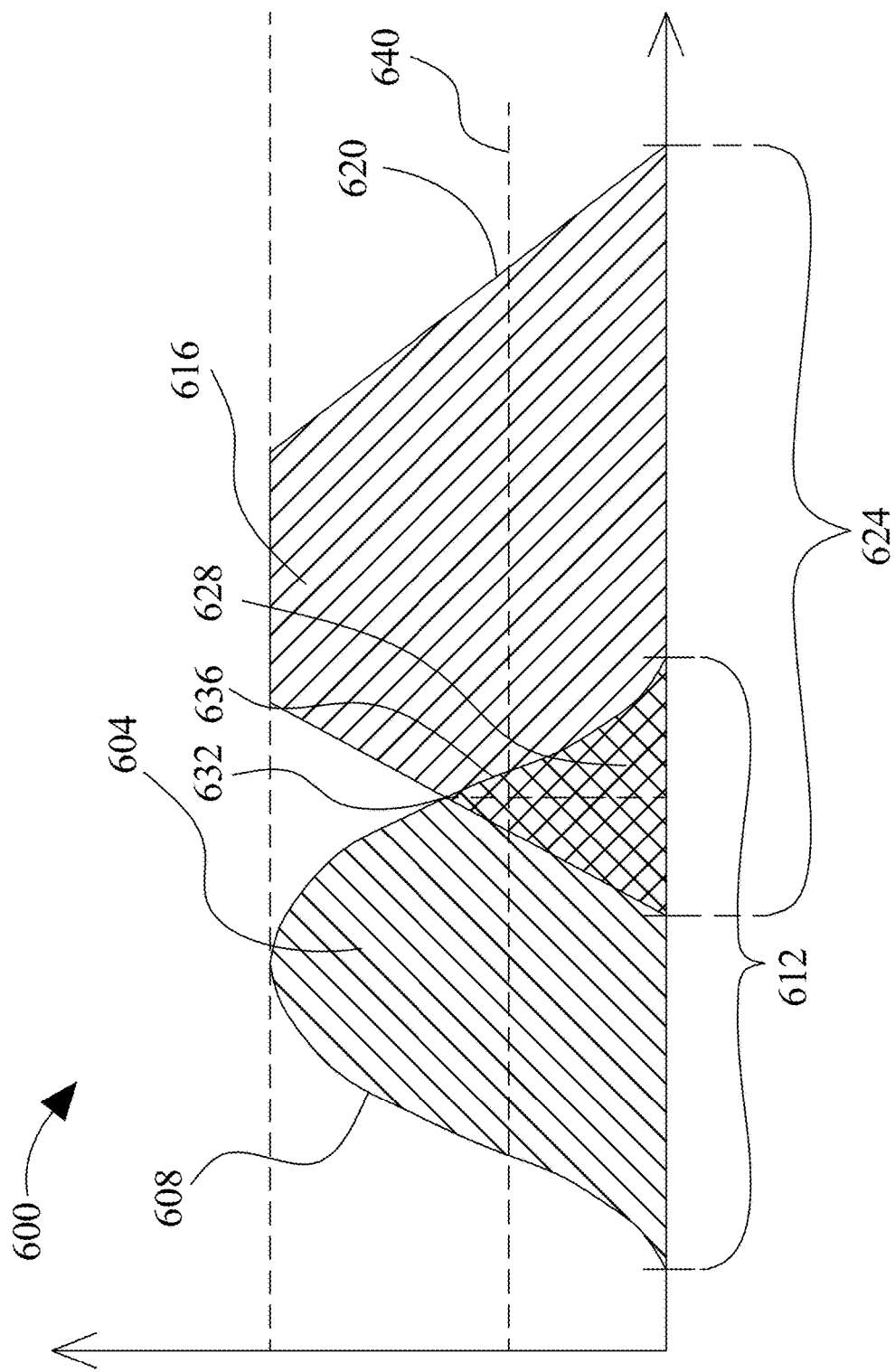
FIG. 6 is a schematic diagram illustrating exemplary embodiments of fuzzy sets.

Referring now to FIG. 6, an exemplary embodiment of fuzzy set comparison 600 is illustrated. A first fuzzy set 604 may be represented, without limitation, according to a first membership function 608 representing a probability that an input falling on a first range of values 616 is a member of the first fuzzy set 604, where the first membership function 608 has values on a range of probabilities such as without limitation the interval [0,1], and an area beneath the first membership function 608 may represent a set of values within first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \le x < b \\ \frac{c-x}{c-b}, \text{ if } b < x \le c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as $$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure. A fuzzy set may include Cartesian products of two or more fuzzy sets as described above.

First fuzzy set 604 may represent any value or combination of values as described above, A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 628 that overlaps, first membership function 608 and second membership function 620 may intersect at a point 632 representing a probability, as defined on probability interval, of a match between first fuzzy set 604 and second fuzzy set 616. Alternatively or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, threshold may indicate a sufficient degree of overlap between fields and/or parameters represented by one or more fuzzy sets and/or Cartesian products thereof for combination to occur as described above. There may be multiple thresholds. Each threshold may be established by one or more user inputs. Alternatively or additionally, each threshold may be tuned by a machine-learning and/or statistical process, for instance and without limitation as described above.

It is to be noted that any one or more of the aspects and embodiments described herein may be implemented using one or more machines. For example, machines such as computing devices that are utilized as a user computing device for an electronic document, one or more server devices, such as a document server, or the like, may be implemented and programmed according to the teachings of this disclosure. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Figure 7:
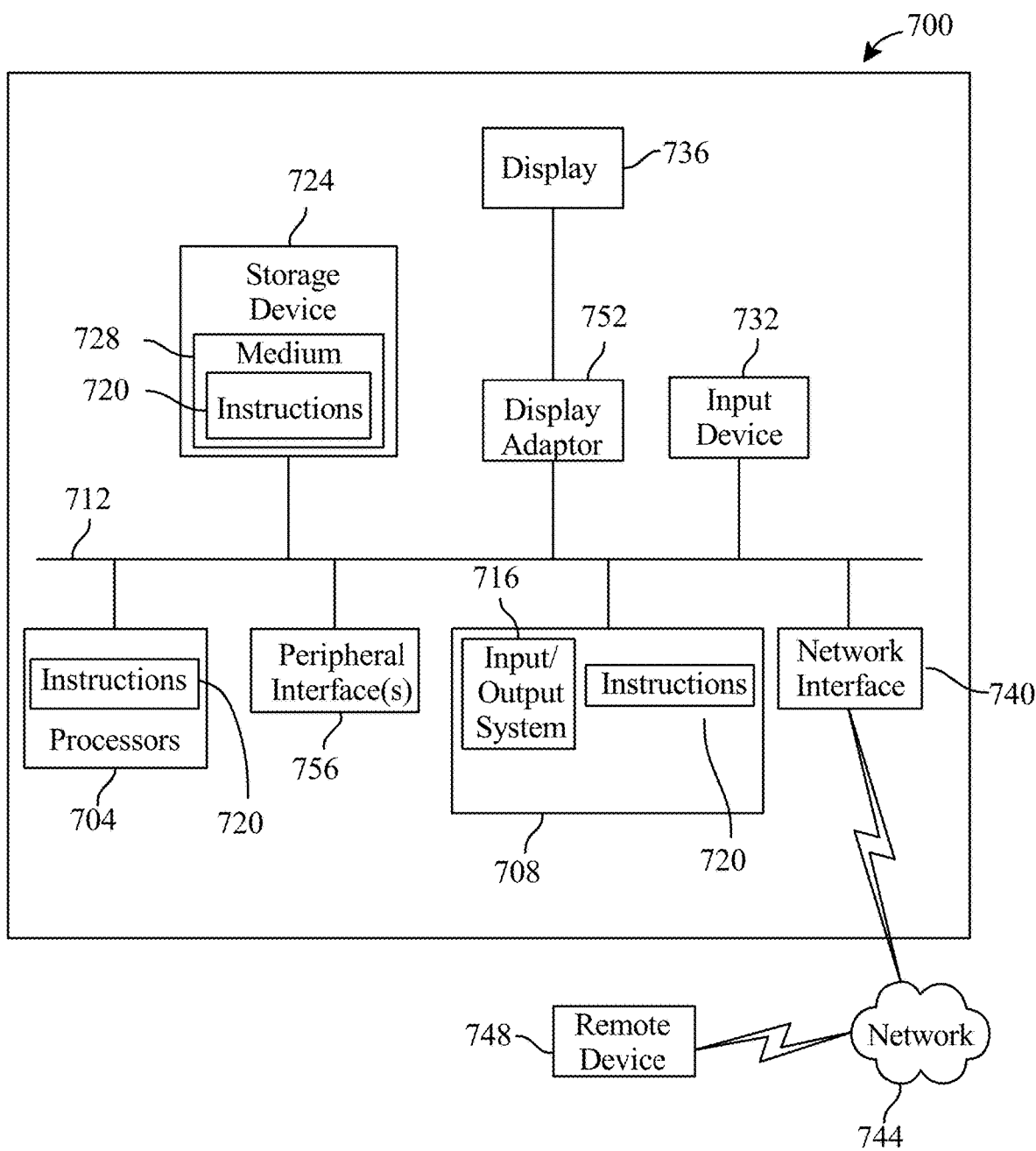
FIG. 7 is a block diagram illustrating a computing system that can be used to implement any one or more of the methodologies disclosed in this disclosure and any one or more portions thereof. The drawings are not necessarily to scale and may be illustrated by phantom lines, diagrammatic representations and fragmentary views. In certain instances, details that are not necessary for an understanding of the embodiments or that render other details difficult to perceive may have been omitted.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, devices, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A programmable pill dispensing device, wherein the device comprises:
    a housing comprising:
        a storage cavity contained within the housing and configured to store a pill;
        a channel, wherein the channel extends from the storage cavity;
        a sensor, wherein the sensor is configured to detect a quantity of pills disposed in the channel; and
        a tray connected to the channel;
    a dispensing element, wherein the dispensing element is at least partially disposed within the channel and configured to dispense the pill when actuated and wherein the dispensing element is a rotation dispensing element which comprises:
        a body, wherein the body may be rotated about a central axis, wherein the central axis is substantially horizontal; and
        a thread extending from the body, wherein a height of the thread is greater than a height of the pill, wherein the thread comprises a plurality of roots and a plurality of flanks, and wherein each root of the plurality of roots are disposed in spaces between adjacent flanks of the plurality of flanks, and wherein the spaces comprise a width, wherein the width captures the pill, such that the pill abuts adjacent flanks of the plurality of flanks; and
    a controller configured to:
        actuate the dispensing element at a predetermined dispensing time; and
        determine when the quantity of pills is less than a predetermined quantity threshold; and
    wherein, upon an actuation, the dispensing element permits the pill to traverse through the channel in a quarter revolution of the body and into the tray for retrieval by a user.

2. The device of claim 1, wherein the predetermined quantity threshold is a function of prescription information.

3. The device of claim 1, wherein the sensor comprises a cell load sensor.

4. The device of claim 1, wherein the controller is further configured to command the device to enter a fail safe mode when a loss of power is detected.

5. The device of claim 4, wherein the fail safe mode requires the use of a security component to access the storage cavity.

6. The device of claim 5, wherein the controller is further configured to send an alert if tampering is detected by a security component while the device is in the fail safe mode.

7. The device of claim 4, further comprising a backup power source, wherein the controller is further configured to switch a power source of the device to the backup power source when a loss of power is detected.

8. The device of claim 1, further comprising a communication component, wherein the communication component communicates the status of the pill to a remote device operated by remote personnel.

9. The device of claim 8, wherein the communication component is configured to notify the remote personnel if the pill has not been retrieved from the tray by the user within a predetermined retrieval time.

10. The device of claim 1, further comprising a fingerprint reader configured to scan a finger of a user to allow access to the tray.

11. A method of automatedly dispensing a pill using a programmable pill dispensing device, the method comprising:
    storing pills in a storage cavity contained within a housing of a programmable pill dispensing device;
    detecting a quantity of pills disposed in the channel using a sensor;
    determining, using a controller, when the quantity of pills is less than a predetermined quantity threshold;
    actuating a dispensing element of the device at a predetermined time using the controller, wherein the dispensing element is a rotation dispensing element which comprises:
        a body, wherein the body may be rotated about a central axis, wherein the central axis is substantially horizontal; and
        a thread extending from the body, wherein a height of the thread is greater than a height of the pill, wherein the thread comprises a plurality of roots and a plurality of flanks, and wherein each root of the plurality of roots are disposed in spaces between adjacent flanks of the plurality of flanks, and wherein the spaces comprise a width, wherein the width captures the pill, such that the pill abuts adjacent flanks of the plurality of flanks; and
    dispensing, upon actuation of the dispensing element, a pill through a channel of the device, which extends from the storage cavity and is connected to a tray of the device, so that the pill traverses through the channel in a quarter revolution of the body and into the tray; and
    alerting a user using an alarm transducer that the pill is dispensed and ready for retrieval by the user.

12. The method of claim 11, wherein the predetermined quantity threshold is a function of prescription information.

13. The method of claim 11, further comprising entering, using the controller, a fail safe mode when a loss of power is detected.

14. The method of claim 13, wherein the fail safe mode requires the use of a security component to access the storage cavity.

15. The method of claim 14, further comprising sending, using the controller, an alert if tampering is detected by a security component while the device is in the fail safe mode.

16. The method of claim 13, further comprising switching, using the controller, a power source of the device to a backup power source when a loss of power is detected.

* * * * *